(12) United States Patent
Webster et al.

(10) Patent No.: US 6,198,953 B1
(45) Date of Patent: Mar. 6, 2001

(54) METHOD AND SYSTEM FOR CONTINUOUS SWEAT COLLECTION AND ANALYSIS

(76) Inventors: Henry L. Webster, 122 E. 700 North, Logan, UT (US) 84321; Wayne K. Barlow, 170 E. 1700 South; Dennis R. Briscoe, 149 E. 200 North, both of Providence, UT (US) 84332; Carmelo G. Quirante, 1225 Eastridge Dr., Logan, UT (US) 84321; Scot B. Thomas, 206 E. Center, Providence, UT (US) 84332

( * ) Notice: Subject to any disclaimer, the term of this patent is extended or adjusted under 35 U.S.C. 154(b) by 0 days.

(21) Appl. No.: 09/266,532

(22) Filed: Mar. 11, 1999

(51) Int. Cl.$^7$ ....................................................... A61N 1/30
(52) U.S. Cl. ................................................................ 600/345
(58) Field of Search ..................................... 600/345, 346

(56) References Cited

U.S. PATENT DOCUMENTS

| | | | |
|---|---|---|---|
| 3,635,213 | * | 1/1972 | LaHay ................................... 600/346 |
| 4,383,529 |   | 5/1983 | Webster ................................. 604/20 |
| 4,542,751 |   | 9/1985 | Webster et al. ....................... 128/760 |
| 5,050,604 | * | 9/1991 | Reshef et al. ........................ 600/346 |
| 5,131,390 | * | 7/1992 | Sakaguchi et al. .................. 600/346 |
| 5,465,713 | * | 11/1995 | Schoendorfer ........................ 600/346 |

* cited by examiner

Primary Examiner—Robert L. Nasser
(74) Attorney, Agent, or Firm—Mallinckrodt & Mallinckrodt; Philip A. Mallinckrodt; Robert R. Mallinckrodt (57) ABSTRACT

The method and system of the invention provide especially for continuously obtaining and analyzing, on a real time basis, sweat from a selected area of skin on the body of a person, especially a neonate, being diagnosed for cystic fibrosis, by causing sweating of the selected area of skin, by placing an electrically positive iontophoretic electrode device of a set of said devices over the selected area of skin preferably within a previously placed receiving and holding device which, following the induction of sweat and removal of the electrically positive iontophoretic electrode device, receives a sweat-sensing electrode device that continuously sends electrical signals to sweat analysis circuitry for providing a digital readout of the ionic composition of the sweat. The receiving and holding device insures recovery and utilization of essentially all of the sweat being produced by the selected area of skin. The sweat-sensing electrode device is of unique construction with respect to the flow of recovered sweat relative to ion-sensing electrodes arranged preferably serially along the path of sweat flow through the body of the sweat-sensing electrode device. The invention is not restricted to the foregoing use, but may be used in whole or in part to analyze sweat on a real time basis however produced and collected, with or without timing of its travel between sequential electrodes and use of the travel time to calculate the rate of sweating within the selected area of skin.

23 Claims, 5 Drawing Sheets

METHOD AND SYSTEM FOR CONTINUOUS SWEAT COLLECTION AND ANALYSIS

BACKGROUND OF THE INVENTION

1. Field

The invention is concerned primarily with the recovering and sensing of sweat induced by iontophoresis for diagnosing the presence of cystic fibrosis in children or adults, especially the heretofore neglected area of obtaining and sensing sweat of newborn infants, but is also concerned with the sensing of sweat however induced or recovered from an area of a person's skin that is usually selected in advance.

2. State of the Art

Webster U.S. Pat. No. 4,383,529 and Webster et al. U.S. Pat. No. 4,542,751, both assigned to Wescor, Inc., Logan, Utah, disclose and describe in detail what have become standard devices and standard procedures for this diagnostic area of medical practice.

Thus, in Webster et al. U.S. Pat. No. 4,542,751 a sweat-collection device having a shallowly concave, sweat-collecting surface is applied to a patient's skin over an area that has been stimulated by iontophoresis. A length of flexible, plastic tubing has one end connected to an axial bore through which such plastic tubing extends for receiving a sample of sweat to be transferred to sweat-analyzing equipment. A strap secured to opposite ends of the sweat-collection device enables such device to be securely held in place against and covering a selected area of skin of a person to be diagnosed, which skin area has been previously subjected to iontophoresis for inducing sweating of that portion of the person's skin.

For iontophoresis prior to application of the above-referenced sweat-collection device, a pair of iontophoretic electrode devices are employed in accordance with Webster U.S. Pat. No. 4,383,529, thereby inducing sweating at the selected area of the person's skin. Such iontophoretic electrode devices may be and usually are mutually similar for convenience, but one is electrically positive for supplying the sweat-causing ions and the other electrically negative for completing an electrical circuit. At least the positive electrode device comprises a receptacle for holding an agar gel disc carrying an iontophoretic drug (usually pilocarpine). The agar gel disc has an exposed surface for contacting the selected area of skin and an opposite surface in electrical contact with an electrically positive electrode, so that the drug is applied to the thereby covered area of skin for stimulating the sweat glands of such area of skin. The other, an electrically negative electrode device, is conveniently the same, except for being electrically negative rather than positive and may be left in place or may be removed following sweat recovery. In any event, the electrically positive electrode device is replaced by the sweat-collecting device of Webster et al. U.S. Pat. No. 4,542,751 for collecting the induced sweat to be analyzed for diagnostic purposes.

SUMMARY OF THE INVENTION

In working to overcome problems posed by attempts to similarly diagnose cystic fibrosis in newly born infants, whose limbs are usually incapable of accommodating the foregoing devices as designed for children and adults, we have developed a new system for applying the sweat-inducing drug to, and for recovering and testing substantially all of the induced sweat from, the limited sweat-producing skin area concerned, so as to effectively cope with the very small amounts of sweat that can be induced in and recovered from neonates.

In accordance with one aspect of the invention, at least one receiving and holding device is provided for, first, receiving and holding the electrically positive iontophoretic electrode device over a selected area of skin of a patient to be induced to sweat, and, then, following removal of such electrically positive iontophoretic electrode device, for receiving and holding the sweat-sensing device over substantially the same area of skin. The electrically positive electrode device is preferably constructed in accordance with Webster U.S. Pat. No. 4,383,529, but is supplied with structure for holding it in place in the receiving and holding device. A second and preferably similar receiving and holding device is provided for receiving and holding a preferably similar but electrically negative iontophoretic electrode device on the skin of the patient adjacent to the selected sweating area to complete the iontophoretic electrical circuit. It is of particular significance that, in accordance with this aspect of the invention, the sweat-sensing electrode device be placed substantially in registry with or substantially completely covering the selected area of the skin in which sweating is induced so as to recover substantially all of the sweat produced. This is especially important in the diagnosing of neonates, because of the limited amount of sweat produced by them, but also constitutes an improvement on the equipment and procedures of the aforementioned Webster et al. patents owned by Wescor, Inc. of Logan, Utah, and marketed by it under the registered trademark "MACRODUCT".

As previously indicated, in accordance with one preferred aspect of this invention a sweat-sensing electrode device having at least two sensing electrodes replaces the electrically positive iontophoretic electrode device following use thereof for iontophoretic purpose. Such sweat-sensing electrode device is provided for continuously determining on a real-time basis the characteristics or properties of sweat entering such sweat-sensing device as the sweat travels progressively therethrough in an elongate and relatively narrow stream from the entry thereof to a discharge therefrom. Contrary to the previous "MACRODUCT" system, our new overall system may and preferably does do away with the elongate, coiled tube for receiving and storing recovered sweat for subsequent analysis and provides a substitute sweat-recovery device as preferably an integrated unit for the continuous flow of sweat therethrough so that real-time analysis of the sweat recovered from the selected area of the patient's skin can be carried out. The sensing electrode or electrodes of the sweat-sensing device is or are arranged for electrical connection with a sweat-analysis module.

The sweat-sensing device is unique in having a body member that is preferably an integrated body that contains an elongate, relatively narrow passage or passages for the continuous flow of sweat from electrical communication (preferably direct contact) with one sweat-sensing electrode to another sweat-sensing electrode as serially arranged, and that such sweat-sensing device is held by the previously-indicated receiving and holding device. This is the best mode presently contemplated for carrying out the present invention, but it should be realized that each feature of the general combination constitutes an inventive subcombination in and of itself and may be used with or without the others. Thus, part or even all of the coiled tube of the sweat-collection device of the prior "MACRODUCT" system could be used along with the receiving and holding device for sequentially receiving, first, an electrically positive, sweat-inducing, iontophoretic electrode device and, then, the unique sweat-sensing electrode device. For example, the "MACRODUCT" system presently used for testing the sweat of adults and small children does not normally require the compactness or continuous real-time testing of the presently disclosed overall system, but could make use of the receiving and holding device disclosed herein.

The unique sweat-sensing electrode device of the present overall combination (and also constituting a subcombination thereof) preferably has a substantially rigid body integrally combining a concave sweat-collecting surface with a relatively narrow, elongate flow passage or passages communicating with serially spaced sensing electrodes for contact by the recovered sweat as it flows by. An entry port for receiving and an exit port for discharging the stream of sweat on a substantially continuous basis are provided so that the sensing electrodes are contacted progressively by the stream of flowing sweat on a substantially continuous basis. Electrical connection of the electrode or electrodes with the sweat analysis module is preferably accomplished by an electrical outlet device plugged onto the body of the sweat-sensing electrode device.

Iontophoresis is preferably controlled by regulating the amount of electrical current fed to the respective electrodes of a pair of sweat-inducing electrode devices, which are conveniently both of the type containing gel discs as shown in the above-referred to Webster U.S. Pat. No. 4,383,529, although it should be realized that it is only a matter of convenience that the negative electrode device is the same as the positive electrode device so both can be received by respective holding devices of the same construction. Sequential use of the same receiving and holding device, for first receiving the electrically positive sweat-inducing electrode device and then the unique sweat-sensing electrode device in substantial registry with the selected area of skin is a great advantage in enabling small quantities of sweat to be recovered substantially without loss, so as to yield reliable diagnostic results for neonates or for other patients.

THE DRAWINGS

Illustrated in the accompanying drawings is an embodiment of the system of the invention presently contemplated to be the best mode of carrying out the present overall invention in actual practice.

In the drawings.

DETAILED DESCRIPTION OF THE ILLUSTRATED EMBODIMENT

Figure 6:
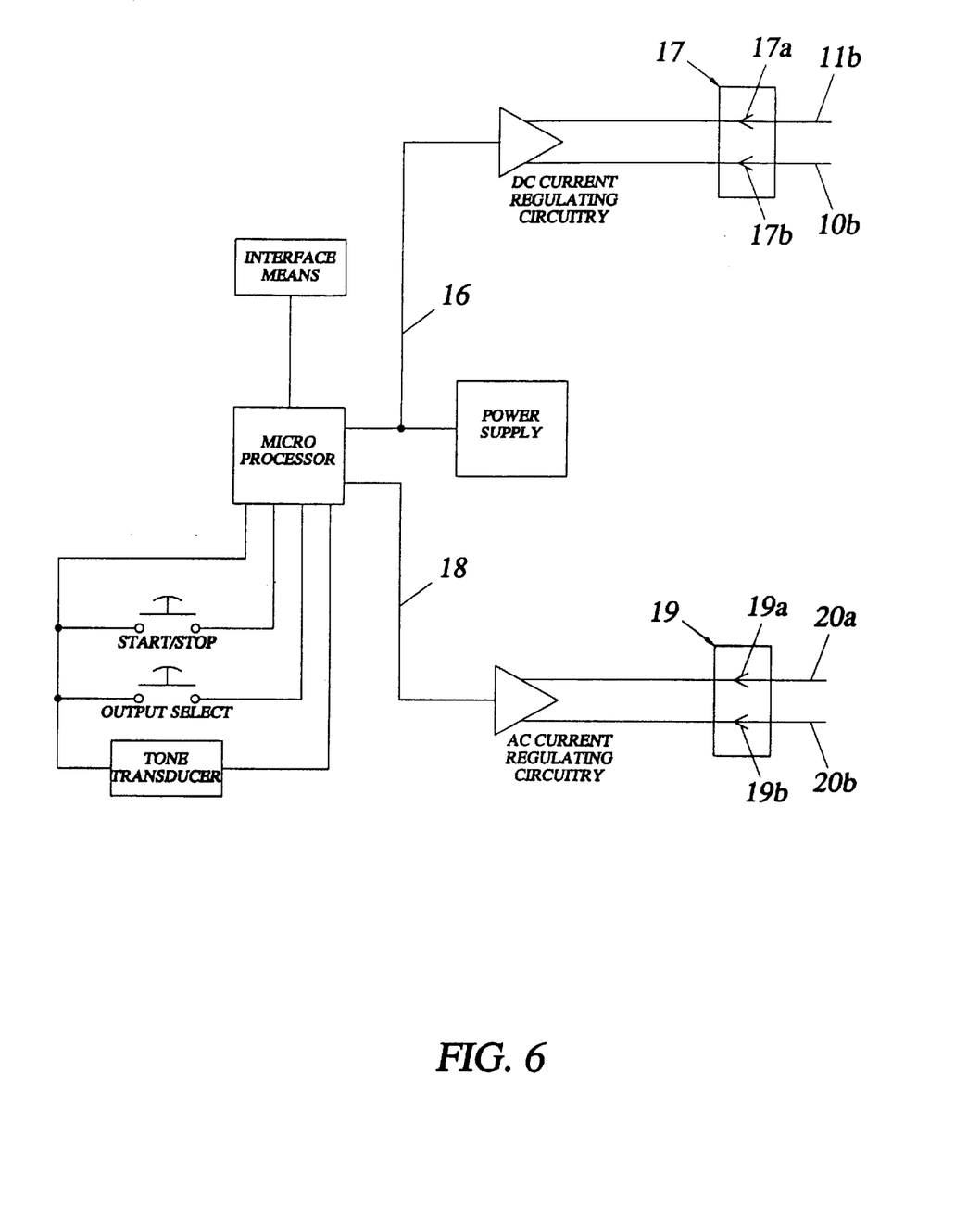
FIG. 6, a combination block and electrical circuit diagram showing, in modular form, the basic system into which are first plugged the iontophoretic electrode devices for iontophoresis of a selected area of skin, and into which the sweat-sensing electrode device is then plugged in to replace, for sweat analysis, the removed electrically positive, iontophoretic electrode device.
Figure 7:
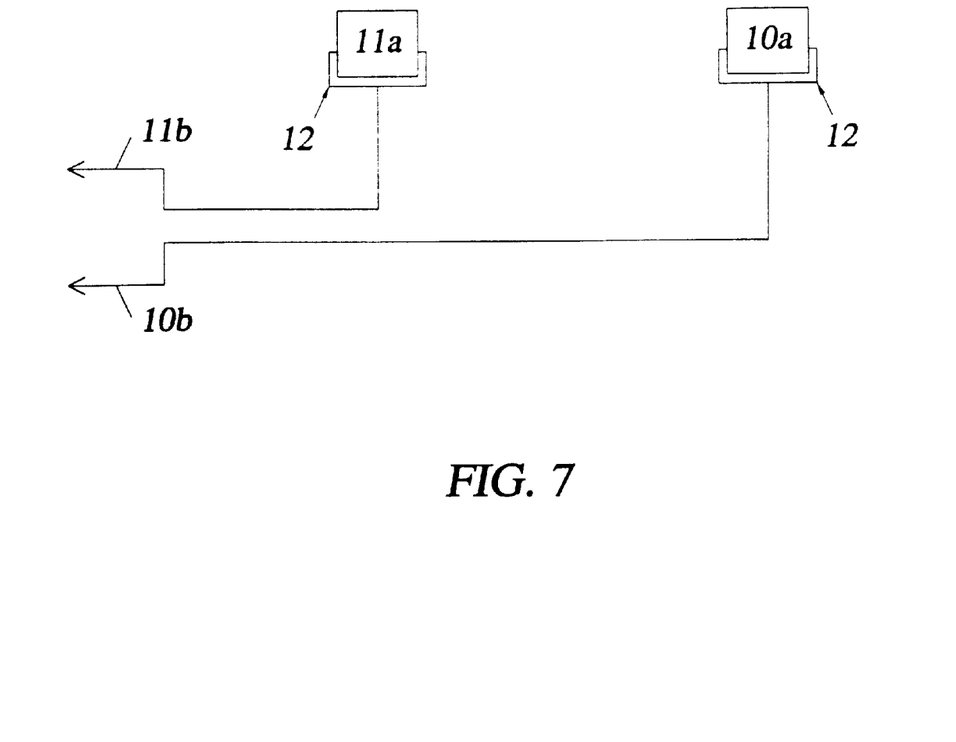
FIG. 7, a similar but more schematic circuit diagram of the iontophoretic portion of the overall system.
Figure 8:
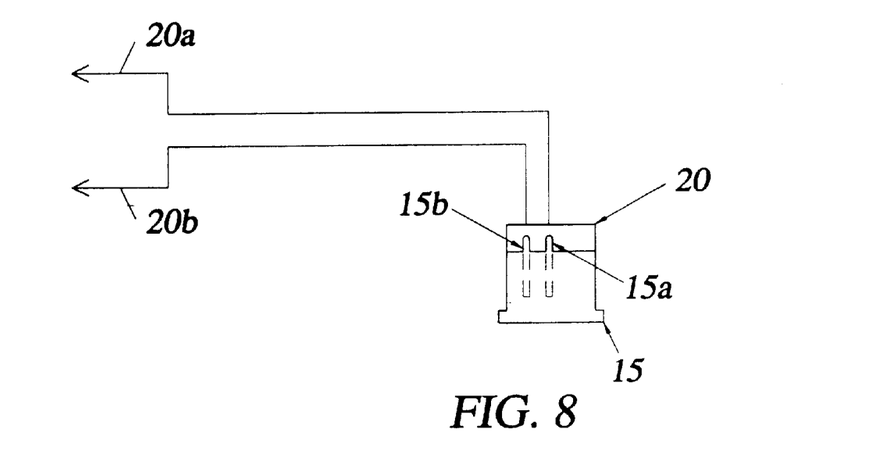
FIG. 8, a corresponding but more schematic circuit diagram of the sweat-sensing portion of the overall system.

The preferred overall system of the invention with respect to inducing sweating by iontophoresis and then sensing and analyzing the induced sweat is shown by the block and circuit diagrams of FIGS. 6–8. FIG. 6 represents the basic electronic module with power supply, microprocessor, users' display, and operating switches, while FIGS. 7 and 8 represent, respectively, auxiliary iontophoresis and sweat-sensor systems, which are selectively plugged into the basic module of FIG. 6 as and when determined by the user.

Figure 1:
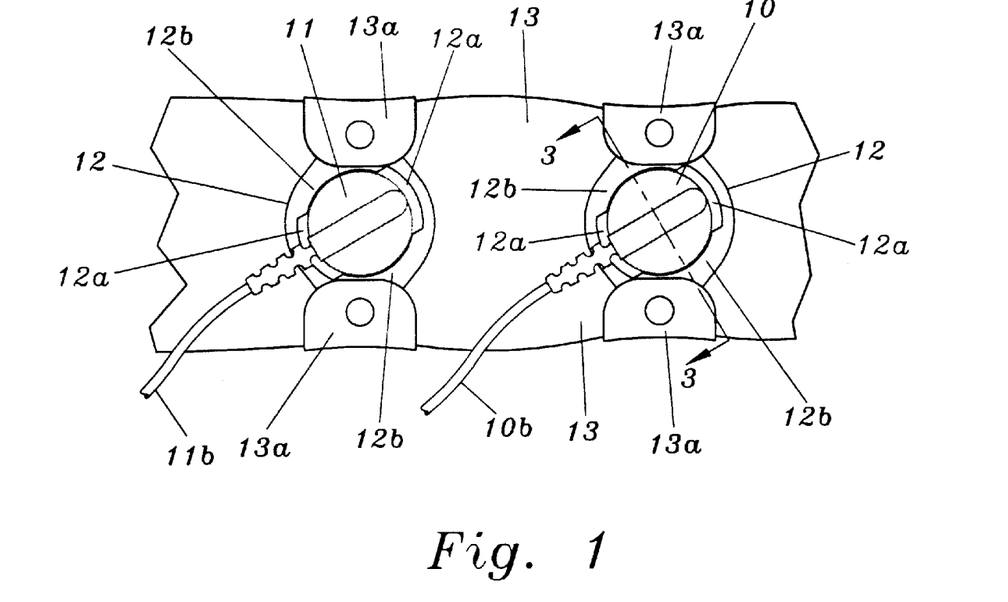
FIG. 1 is a fragmentary top plan view of the iontophoretic part of the system as applied to a patient at the beginning stage of the procedure.
Figure 3:
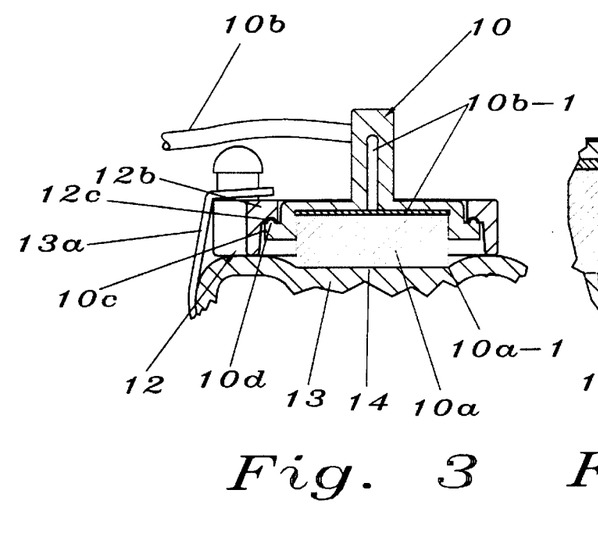
FIG. 3, a view in transverse vertical section taken along the line 3—3 of FIG. 1 through the electrically positive, iontophoretic device and shown partially in elevation, the view being drawn to a considerably larger scale than is that of FIG. 1.

In using the overall system for diagnostic purposes, the sweat-producing auxiliary system of FIG. 7 (with the iontophoretic electrode devices of FIG. 1) is plugged into the basic module of FIG. 6. As shown in FIGS. 1 and 3, the sweat-inducing portion of the overall system includes an electrically positive, iontophoretic electrode device 10, which is preferably similar to the previously mentioned, iontophoretic electrode device of the Webster U.S. Pat. No. 4,383,529 whose hydrophilic and hydrated gel disc 10a contains the sweat-producing drug pilocarpine. An electrical cable connection 10b is provided leading from the positive side of the basic module of FIG. 6.

Figure 2:
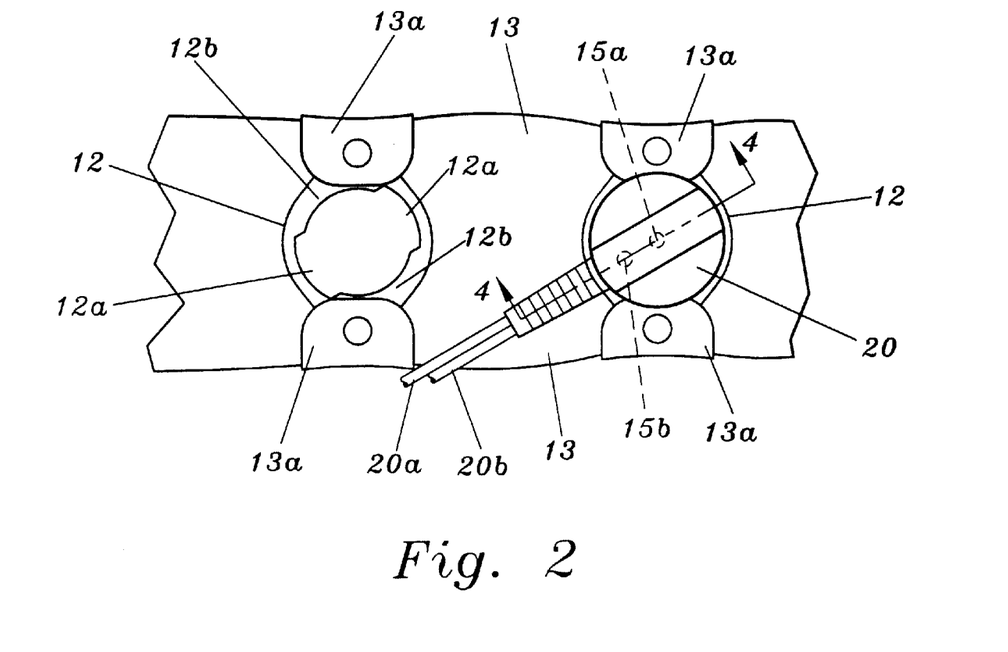
FIG. 2, a corresponding view of the system after replacement of the electrically positive iontophoretic electrode device by the sweat-sensing electrode device of the invention and removal of the no longer necessary, electrically negative iontophoretic electrode device.
Figure 3A:
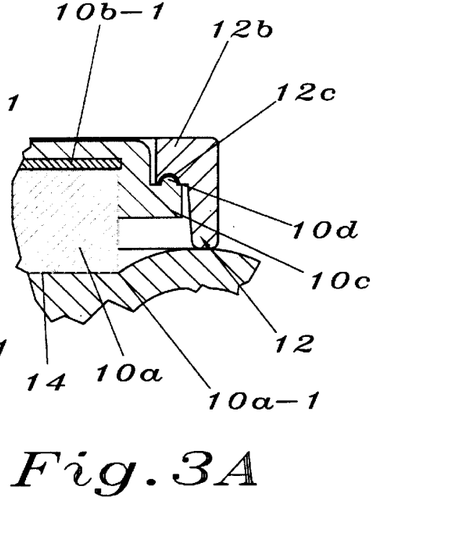
FIG. 3A, a portion of FIG. 3 drawn to a considerably larger scale than is that of FIG. 3.

Such sweat-producing portion of the overall system may also include an electrically negative, iontophoretic electrode device 11, which, for convenience, may correspond to the electrically positive, iontophoretic electrode device and, either with or without the sweat-producing drug in its gel disc 11a, FIG. 7, which corresponds to the gel disc 10a, FIGS. 3, 3A, and 7, and has a gel-disc-covering electrode (not shown) corresponding to the electrode 10b-1 of FIGS. 3 and 3A. However, it may be constructed in any manner, so long as it provides a connection, such as electrical cable 11b, FIG. 1, leading to the negative side of the basic module of FIG. 6. As shown, it preferably fits into one of a pair of substantially rigid, annular receiving and holding devices 12, 12, FIGS. 1 and 2, provided by the present invention and being preferably of molded plastic. If it is constructed merely to provide a negative connection, irrespective of where it is placed, the electrode thereof may be connected in any way to the patient's body, and only a single receiving and holding device 12 need be provided for receiving the electrode device 10.

As shown in FIG. 1, if a pair 12, 12 of the receiving and holding devices is placed along a portion of a patient's body, preferably along a limb 13 thereof, such as an arm of a newborn infant who is professionally referred to as a "neonate", the individual devices 12, 12 are placed on the patient so that one holding device receives the electrically positive, iontophoretic device 10 to cover a selected area of skin 14, FIGS. 3 and 3A, within which sweat is to be generated.

In the illustrated instance, each of the iontophoretic electrode devices 10 and 11 of FIG. 1 is provided with a pair of externally extending, preferably elongate latching flanges (see the latching flanges 10c, 10c, FIG. 3) for introduction into the corresponding receiving and holding device 12 through sets of corresponding arcuate and elongate, receiving marginal recesses 12a, 12a, FIG. 1 (and see particularly the left-hand side of FIG. 2), provided in inwardly extending and overhanging rims of the devices 12, 12, which rims are thereby divided into respective pairs or sets of individual latching flanges 12b, 12b.

Following insertion of the iontophoretic electrode devices 10 and 11 into the respective receiving and holding devices 12, 12, as placed on the limb 13 of the patient concerned and held thereon as by respective straps 13a, they are preferably latched securely in place by rotation thereof within such receiving and holding devices 12, 12 until corresponding pairs of latching pins (see the latching pins 10d, 10d in FIGS. 3 and 3A as carried by and extending upwardly from the upper faces of the latching flanges 10c, 10c) click into corresponding pairs of latching keeper recesses (see 12c, 12c, FIGS. 3 and 3A) in the underfaces of the overhanging latching flanges 12b, 12b.

For inducing sweating within the skin area 14, FIGS. 3 and 3A, either substantially in registry with the electrode device 10 or bounded by the inside circumference of the receiving and holding device 12 concerned, electrical power is supplied by any suitable power supply, indicated as such in FIG. 6, as, for example, a battery, through electrical connections, usually on one or more printed circuit boards, as shown schematically at 16, FIG. 6, by way of the indicated DC current-regulating circuitry, to a plug-in facility 17 for electrical cables 10b and 11b of iontophoretic electrode devices 10 and 11, respectively, electric power being also supplied to a microprocessor.

Figure 4:
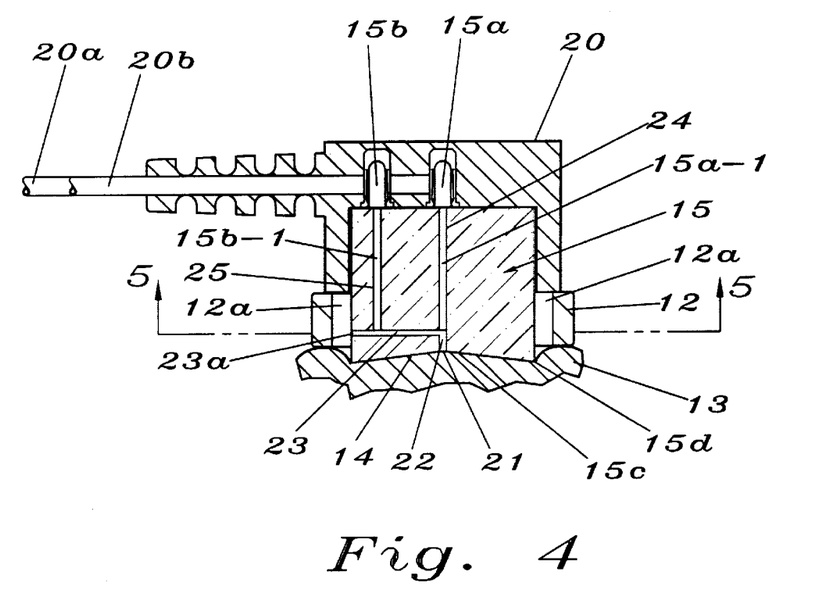
FIG. 4, a similar but longitudinal view in vertical section taken along the line 4—4 of FIG. 2, but drawn to a considerably larger scale than is that of FIG. 2 and on a somewhat larger scale than is that of FIG. 3.

Similarly, electrical power is supplied through similar electrical connections, shown schematically at 18, FIG. 6, by way of the indicated AC current-regulating circuitry to a plug-in facility 19 for electrical cables 20a and 20b, FIG. 6, of an electrical outlet device 20, FIGS. 4 and 8, which is, for convenience, removably associated with sweat-sensor electrode device 15 as an electrical outlet plug for plug-in engagement with and over the body member of such device 15.

Both the positive and negative iontophoretic electrode devices 10 and 11, and sweat-sensing electrode device 15 through its electrical outlet plug device 20, are electrically tied into the basic electronic module of FIG. 6.

Plug-in facility 17 as here shown in FIG. 6 includes plug-in connections 17a and 17b for cables 11b and 10b, respectively, FIG. 7. Plug-in facility 19, FIG. 6, includes plug-in connections 19a and 19b for cables 20a and 20b, respectively, FIG. 8, of electrical outlet device 20 as plugged into and over the body of sweat-sensor electrode device 15, see FIG. 4.

The microprocessor circuitry comprises controller, memory, decoding, and other circuits (not shown but well known to those skilled in the art) for, among other functions, regulating the supplying of electric current as required to induce the desired sweat sample, for measuring the current passing through the sample, and for converting the measurement to digital information. As part of the basic module of FIG. 6, interface means are provided for supplying, for example, alphanumeric display measurements, time, and other desired information. A keyboard may also be provided, as is well known, including, as indicated in FIG. 6, switches for starting and stopping the system and for selecting output from a tone transducer, so that an operator can start and stop and otherwise control the various functions of the system.

As previously indicated, inducement of sweating is the first of two sequential procedures, the second being collection of sweat from the selected skin area 14 after sweating has been induced. For this purpose, the sweat-sensing electrode device 15 is preferably latched into position in that receiving structure 12 from which electrically positive sweat-inducing device 10 has been removed following about two minutes of sweat stimulation throughout what, in accordance with the invention, can be an unusually small area of skin, for example, 2.5 square centimeters. By reason of the receiving and holding device 12, substantially precise registration of sweat-sensing electrode device 15 with the selected area 14 of sweating skin, or at least substantially complete coverage thereof, is assured.

Figure 5:
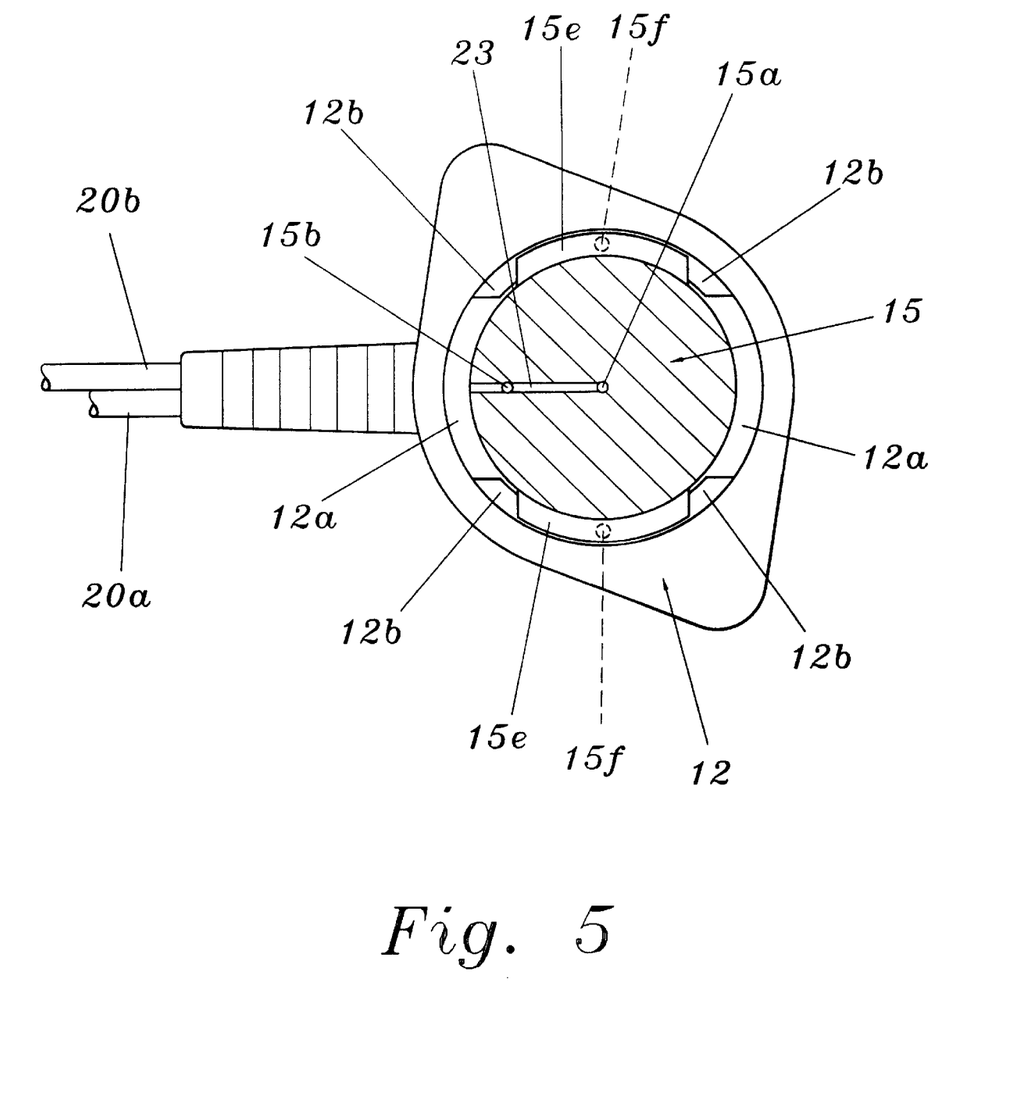
FIG. 5, a view in horizontal section taken along the line 5—5 of FIG. 4 and drawn to a considerably larger scale than is that of FIG. 4.

A latching arrangement similar to that provided for the iontophoretic electrode devices 10 and 11 and the receiving and holding device 12,12 is preferably provided between a set of latching flanges 15e, 15e, FIG. 5, of sweat-sensing electrode device 15 and its receiving and holding device 12. Thus, upstanding latching pins 15f, 15f are provided for co-action with latching recesses 12c, 12c of the receiving and holding device 12 concerned, so that there is minimal, if any, loss of sweat from such selected area of skin. This is very important when testing neonates and has also been found to be advantageous in the testing of children and adults by the "MACRODUCT" system.

A feature of the present invention is a unique construction for the sweat-sensing device 15 as shown in FIGS. 4 and 5, which permits elimination of the long sweat collection and storage tube of the "MACRODUCT" system and enables continuous handling and analysis of recovered sweat on a real-time basis.

Thus, as shown in FIGS. 4 and 5, sweat-recovery device 15 is preferably a body member molded integrally from polystyrene or similar plastic material to provide a broad, shallowly concave, sweat-recovering surface 15c, whose skin-contacting rim 15d (like the rim 10a-1, FIG. 3, of gel disc 10a) substantially forms a seal with the skin about the selected skin area 14 so as to direct the secreted sweat through an entry port 21 at the apex of the concavity and through a passage 22 that extends preferably axially from such entry port 21 of the sweat-recovering surface 15c to intersect a passage 23 that terminates in a discharge port 23a for sweat flowing therethrough. Located in passages 24 and 25, that are spaced apart along elongate passage 23 and that intersect such passage 23, are lower portions 15a-1 and 15b-1, FIG. 4, of the sweat-sensing electrodes 15a and 15b that confront the interior of passage 23.

Such sweat-sensing electrodes sense electrical conductivity of the sweat flowing into and through passage 23, but other kinds of ion-sensing electrodes, as, for example, electrochemical sensors, could be employed along with such changes in the electrical system as may be necessitated thereby, something that is within the skill of the technical arts concerned.

The sweat flow passage 23 terminates externally of the body member of sweat-sensing electrode device 15, as at 23a, for the continuous discharge of the flowing sweat, electrical measurement of which has taken place on a continuous, real-time basis by contact of such flowing sweat with the lower parts 15a-i and 15b-1 of the elongate, spaced-apart, and serially arranged sensing electrodes 15a and 15b.

As previously explained, the body member forming the sweat-sensing electrode device 15 preferably carries removable electrical outlet 20, FIG. 4, as a separable plug-in device. Also, such body member is equipped with the oppositely arranged and externally directed latching flanges 15e, 15e, FIG. 5, corresponding to the latching flanges 10c, 10c of the electrically positive iontophoretic electrode device 10, and with upstanding latching pins 15f, 15f corresponding to the pins 10d, 10d of the electrode device 10 for latching cooperation with the latching keeper recesses 12c, 12c provided by the particular receiving and holding device 12 concerned.

In the sweat-inducing mode, the current source is electrically connected to the sweat-inducing electrodes 10 and 11, which, together with the hydrated gel and the skin of the subject, form a complete circuit for iontophoretic transfer of pilocarpine to the sweat glands in the skin.

In the sweat analysis mode, the current source is electrically connected to the lower parts 15a-1 and 15b-1 of the sweat-sensing electrodes 15a and 15b. The sweat sample itself, between the sweat-sensing electrodes, forms a part of the circuit, whose conductivity varies according to the electrolyte concentration of the sample. The analysis circuitry preferably tests the conductivity of sweat flowing through passage 23 by measuring electrical response to current passed through the flowing sweat, but other ion-sensing electrodes could be employed within the skill of technicians in the arts concerned, as has been previously indicated.

For example, in FIG. 4, either electrode 15a or 15b and its downward extension 15a-1 or 15b-1 could be replaced by an ionspecific electrode, preferably specific for either chloride or sodium, using the other electrode as an electrical ground, the circuit thus formed would then employ electrochemical means to continuously measure the concentration of the selected ion in the sweat flowing through the passage 23. This would be an alternative to measuring electrical conductivity, which unspecifically measures the total ionic concentration of the sweat.

Although the sweat-sensing electrode device 15 is shown in its presently preferred form as a wholly integral body, other ways of constructing it will occur to those skilled in the art, for example, by providing a main body having an open groove which is closed by an overlying cover.

It should also be understood that various aspects of the present invention could be used independently, or with other sweat recovering and measuring systems, for sweat produced by a person.

Thus, in the present system utilizing iontophoretic electrodes, the electrically negative electrode 11 may be left in place to act as an electrical ground reference, or it may be replaced by a different device making electrical contact with the skin of the person concerned. This allows the sweat analysis circuitry to identify the point in time at which the flowing stream of sweat contacts a first electrode of the sweat-sensing device 15. By comparing this time with the point in time at which the flowing stream of sweat reaches a subsequent electrode, the rate of sweat production can be electrically computed and displayed using the known volume of the sweat flowing between the electrodes and the known sweat-collection area of the skin 14 of the person being treated.

Accordingly, the invention provides method and means for determining the rate of sweating of an area, usually preselected, of a person's skin in any given instance by recovering the sweat produced by said area of skin; flowing such sweat between separate electrical conductivity sensing electrodes; timing the flow of the volume of sweat between such electrodes; and using the time to calculate the rate of sweating of such selected area of skin regardless of what causes the sweating, for example physical exercise.

Also, the invention provides method and means for collecting sweat from an area of the skin of a person, regardless of how such area of skin is caused to sweat, and examining the collected sweat to determine a condition of the body of the person that is desired to be known.

Whereas this invention is here illustrated and described with reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A method for obtaining and analyzing sweat from a selected area of a person's skin in the substantial absence of air, comprising causing said area of skin to sweat; recovering the sweat from said area of skin substantially continuously as it is produced by flowing it substantially continuously as an elongate and relatively narrow stream into and through electrical ion-sensing means to discharge exteriorly thereof; and electrically monitoring said ion-sensing means substantially continuously to produce electrical output signals indicative of variations in the ion concentration of said stream of flowing sweat on a real-time basis.

2. A method according to claim 1, wherein the step of monitoring the ion-sensing means comprises measuring electrical conductivity of the recovered sweat.

3. A method according to claim 1, wherein the step of monitoring the ion-sensing means comprises sensing the concentration of a particular species of ion in the sweat.

4. A method according to claim 1, further comprising using the electrical output signals to produce an information display indicative of the condition of the person with respect to the presence or absence of cystic fibrosis.

5. A method according to claim 1, wherein the area of skin is caused to sweat by a set of positive and negative iontophoretic electrode devices; placing the positive one of which devices over the said area of skin and operating it; and recovering the resulting sweat substantially continuously by replacing the positive iontophoretic electrode device with a sweat-sensing electrode device containing said ion-sensing means.

6. A method according to claim 5, wherein the sweat-sensing electrode device is a body having a concave sweat-recovering surface and an elongate and relatively narrow passage extending through said body from a sweat-entry end at the apex of said sweat-recovering surface to a discharge end for sweat; and wherein the ion-sensing means comprises electrical ion-measuring electrodes positioned serially along said passage in communication therewith.

7. A method according to claim 5, wherein is included the step of securing a receving and holding device over the area of skin for sequentially receiving and holding, first, the electrically positive, iontophoretic electrode device and, then, the sweat-sensing electrode device in sequentially the same registry with said area of skin; sequentially mounting and seuring, first, the electrically positive, iontophoretic electrode device and, then, the sweat-sensing electrode device in said receiving and holding device; and sequentially operating the respective electrode devices.

8. A method according to claim 7, wherein the receiving and holding device and the electrode devices themselves are provided with interlatching members for holding said electrode devices in place in said receiving and holding device; and sequentially placing the respective electrode devices in and interlatching them with said receiving and holding device.

9. A method for obtaining and analyzing sweat from a selected area of a person's skin, comprising causing said area of skin to sweat; recovering the sweat from said area of skin substantially continuously; flowing the recovered sweat substantially continuously through electrical ion-sensing means; and electrically monitoring said ion-sensing means substantially continuously to produce electrical signals indicative of variations in ion concentration of the flowing sweat on a real-time basis, wherein the electrical signals indicative of variations in the flowing sweat are monitored by analyzing means, which are electrically associated with electrical control means for sweat induction in respective circuit portions of microprocessor circuitry in common, which circuitry has a manually operated microprocessor; and operating said microprocessor to activate the respective circuit portions sequentially to proved a first electrical output and a second electrical output; sending said first electrical output form the sweat induction circuit portion to said electrical control means for regulating the strength of sweat induction; and sending said second electrical output form the other circuit portion to said ion-sensing means for analyzing the recovered sweat from said area of the person's skin.

10. A method according to claim 9, wherein the ion-sensing means comprise a pair of electrically conductive, sensing electrodes serially spaced apart along and in communication with the path of flow of the recovered sweat; wherein the sensing electrodes are monitored by measuring the time of flow of the flowing sweat between a sensing electrode of said pair and the subsequent sensing electrode of said pair; and using the measurements so obtained, along with the known volume of sweat flowing between the electrodes and the known size of the selected area of skin to obtain the rate of sweating by the person.

11. A system for obtaining and analyzing sweat from a selected area of a person's skin in the substantial absence of air, comprising iontophoretic means for causing a selected area of skin of the person to sweat; means for recovering sweat from said selected area of skin substantially continuously as produced by the sweat glands of said area of skin, which sweat-recovery means comprises a body member having an elongate and relatively narrow passage with an entry end and a discharge end; electrical ion-sensing means confronting the interior of said passage for contact by the recovered sweat as it flows as a substantially continuous stream through said passage past and in contact with said ion-sensing means to produce electrical signals indicative of variations in the ion concentration of the flowing sweat on a real-time basis.

12. A system according to claim 11, wherein are included means for using the resulting electrical signals to provide information indicative of the condition of the person with respect to the presence or absence of cystic fibrosis.

13. A system according to claim 11, wherein the electrical ion-sensing means are electrical conductivity sensing electrodes.

14. A system according to claim 11, wherein the electrical ion-sensing means comprises at least one electrochemical sensor producing electrical signals in proportion to the concentration of a particular species of ion in the sweat.

15. A system according to claim 11, wherein the means for causing a selected area of skin on the body of a person to sweat comprises an electrically positive, iontophoretic, drug-carrying, electrode device and an electrically negative, electrode device for completing an iontophoretic electrical circuit; and wherein the means for recovering sweat from the said selected area of skin substantially continuously, the ion-sensing electrode means, and the means for flowing the recovered sweat substantially continuously through said ion-sensing means are provided by a sweat-sensing electrode device.

16. A system according to claim 15, wherein is included a device for sequentially receiving and holding the electrically positive iontophoretic, drug-carrying electrode device and the sweat-sensing electrode device in substantially the same registry with the selected area of skin.

17. A system according to claim 15, wherein the receiving and holding device and the electrode devices themselves are provided with interlatching members for holding said electrode devices in place over the selected area of skin.

18. A system according to claim 8, wherein the sweat-sensing electrode device comprises a body member having a concave sweat-recovering surface and an elongate and relatively narrow passage leading through said body member from the apex of said sweat-recovering surface to a discharge passage for sweat; and wherein the sweat-sensing electrode device comprises electrical conductivity measuring electrodes positioned serially in communication with said passage.

19. A system according to claim 18, wherein is included an electrical outlet plug device adapted to be plugged into the body member of the sweat-sensing electrode device in electrical contact with the electrodes thereof.

20. A method for the continuous recovery and analysis of sweat from a person, comprising sealingly applying against the absence of air to a selected area of skin of the person a sweat-sensing electrode device having a body member with an exterior surface adapted to cover said selected area of skin and with an elongate and relatively narrow passage having a sweat-receiving end opening into said exterior surface for receiving sweat therefrom substantially immediately as it is produced by the sweat glands of said area of skin to provide a substantially continuously flowing, elongate and relatively narrow stream of sweat, there being at least a pair of electrodes with sweat-sensing ends confronting the interior of said passage and arranged serially along said passage so the received sweat flowing in and through said passage as a substantially continuous stream will pass from electrode to electrode between and in contact therewith providing electrical output from which is obtained an ion concentration verses time profile that varies as freshly produced sweat is added to the flowing stream; and using the electrical output from said electrodes substantially continually to present said profile on a real-time basis.

21. A system for the continuous recovery and analysis of sweat from a selected area of skin of a person in the substantial absence of air, comprising a sweat-sensing device with a body member having an exterior surface adapted to sealingly cover the selected area of skin and having an elongate and relatively narrow passage with a sweat entry end opening into said exterior surface for receiving sweat therefrom substantially immediately as it is produced by the sweat glands of said area of skin to provide a substantially continuously flowing, elongate and relatively narrow stream of sweat, there being at least a pair of electrodes with sweat-sensing ends confronting the interior of said passage and arranged serially along said passage so the received sweat flowing in and through said passage as a substantially continuous stream will pass from electrode to electrode between and in contact therewith providing electrical output from which is obtained an ion concentration verses time profile that varies as freshly produced sweat is added to the flowing stream; and means for analyzing the electrical output from said electrodes substantially continually to present said profile on a real-time basis.

22. A system for attachment to the body of a person to obtain and analyze sweat from a selected area of the skin of said person in the substantial absence of air, comprising iontophoretic means for causing said selected area of skin to sweat; means for directing the sweat, that emerges substantially continuously under hydraulic pressure from the seat glands of said selected area of skin, into the entry end of an elongate and relatively narrow passage which has a discharge end and electrical ion-sensing means confronting the inside of such flow passage, so the sweat will flow through said passage in contact with said electrical ion-sensing means; and means for using electrical signals from said ion-sensing means to provide, on a substantially continuous basis during said sweat production, diagnostic information indicative of the condition of the person with regard to the presence or absence of cystic fibrosis.

23. A method for determining the rate of sweating of a living body comprising causing, in the substantial absence of air, a selected area of a person's skin to sweat, recovering the sweat from said area as it is produced by flowing it substantially continuously as an elongate and relatively narrow stream into and through electrical sensing means to discharge exteriorly thereof, and electrically monitoring said ion sensing means substantially continuously to produce electrical output signals indicative of the rate of sweating of said area, and determining the rate of sweating from said signals.

* * * * *